US006997950B2

(12) United States Patent
Chawla

(10) Patent No.: US 6,997,950 B2
(45) Date of Patent: Feb. 14, 2006

(54) VALVE REPAIR DEVICE

(76) Inventor: Surendra K. Chawla, 26 Balfour Dr., West Hartford, CT (US) 06117

( * ) Notice: Subject to any disclaimer, the term of this patent is extended or adjusted under 35 U.S.C. 154(b) by 16 days.

(21) Appl. No.: 10/345,750

(22) Filed: Jan. 16, 2003

(65) Prior Publication Data

US 2004/0143323 A1 Jul. 22, 2004

(51) Int. Cl.
A61F 2/24 (2006.01)
(52) U.S. Cl. .................... 623/2.1; 623/13.11; 606/151
(58) Field of Classification Search ............... 623/2.1, 623/2.11–2.19, 2.36, 2.4, 13.11; 606/151, 606/139, 228, 213, 232
See application file for complete search history.

(56) References Cited

U.S. PATENT DOCUMENTS

| | | | | |
|---|---|---|---|---|
| 3,130,418 A * | 4/1964 | Head et al. | ............... | 623/2.12 |
| 4,960,424 A | 10/1990 | Grooters | ................... | 623/2 |
| 5,415,667 A * | 5/1995 | Frater | ................... | 623/2.11 |
| 5,554,184 A | 9/1996 | Machiraju | ................. | 623/2 |
| 5,662,704 A * | 9/1997 | Gross | ................... | 623/2.1 |
| 6,074,417 A | 6/2000 | Peredo | ..................... | 623/2 |
| 6,143,025 A | 11/2000 | Stobie et al. | ............... | 623/2.39 |
| 6,312,447 B1 | 11/2001 | Grimes | ................... | 606/219 |
| 6,332,893 B1 | 12/2001 | Mortier et al. | ............... | 623/2.36 |
| 6,338,240 B1 | 1/2002 | Endo et al. | ................. | 60/39.03 |
| 6,350,282 B1 | 2/2002 | Eberhardt | ................. | 623/2.13 |
| 6,358,277 B1 | 3/2002 | Duran | .................... | 623/2.12 |
| 6,409,759 B1 * | 6/2002 | Peredo | ................... | 623/2.13 |
| 6,726,715 B1 * | 4/2004 | Sutherland | ................. | 623/2.1 |
| 6,764,510 B1 * | 7/2004 | Vidlund et al. | ............... | 623/2.34 |
| 6,797,002 B1 * | 9/2004 | Spence et al. | ............... | 623/2.38 |
| 2003/0105519 A1 * | 6/2003 | Fasol et al. | ................. | 623/2.1 |
| 2004/0106989 A1 * | 6/2004 | Wilson et al. | ............... | 623/2.11 |
| 2004/0122513 A1 * | 6/2004 | Navia et al. | ................. | 623/2.12 |
| 2004/0138745 A1 * | 7/2004 | Macoviak et al. | ............. | 623/2.36 |
| 2005/0010287 A1 * | 1/2005 | Macoviak et al. | ............. | 623/2.36 |
| 2005/0107871 A1 * | 5/2005 | Realyvasquez et al. | ..... | 623/2.11 |

OTHER PUBLICATIONS

"Long-Term Results of Mitral Valve Repairs for Myxomatous Disease With and Without Chordal Replacement With Expeanded Polytetrafluoroethylene Sutures"; Authors: Tirone e, David, MD, Ahmad Omran, MD, Susan Armstrong, MSc, Zhao Sun, PhD, Joan Ivanov, MSc; pp. 1279-1286; The Jornal of Thoracic and Cardiovascular Surgery; Jun. 1998.

* cited by examiner

Primary Examiner—Corrine McDermott
Assistant Examiner—Cheryl Miller
(74) Attorney, Agent, or Firm—Cantor Colburn LLP

(57) ABSTRACT

A valve repair device and method of repair for the mitral valve of the heart is disclosed. The valve repair device includes a leaflet portion, a muscle portion, and a plurality of chords connecting the leaflet portion to the muscle portion. The valve repair device is attached to the diseased valve by suturing the leaflet portion to the affected leaflet and suturing the muscle portion to the affected muscle. The leaflet portion and muscle portion are constructed of cloth made from expanded polytetraflouroethylene. The chords are sutures also constructed from expanded polytetraflouroethylene. The suture position for the muscle portion is determined by positioning the valve repair device adjacent to a normal marginal chord. The valve repair device may be employed to repair the anterior leaflet or posterior leaflet of the mitral valve.

20 Claims, 14 Drawing Sheets

VALVE REPAIR DEVICE

BACKGROUND OF THE INVENTION

The present disclosure relates to a valve repair device and a method for repairing a heart valve. More particularly, this disclosure relates to a valve repair device useful in the repair of the mitral valve.

The human heart has four chambers and four one way valves. The right upper chamber, known as the right atrium, receives deoxygenated blood from the body and passes the blood to the right lower chamber, known as the right ventricle, through the tricuspid valve. The blood then passes through the pulmonary valve and is carried via the pulmonary arteries to the lungs for oxygenation. After the blood is oxygenated, it is received into the left side of the heart. The upper chamber, known as the left atrium, receives the blood from the lungs by four pulmonary veins, two from each lung. The blood is then passed to the left ventricle through the mitral valve. The main pumping chamber, the left ventricle, then pushes the blood to the body through the aortic valve.

The mitral valve is also known as a bicuspid valve, as it has two cusps or leaflets. The leaflets consist of the anterior leaflet, which is located adjacent to the aortic valve, and the posterior leaflet. The anterior leaflet is larger than the posterior leaflet. At the junction of the leaflets, each leaflet has a scalloped edge with three rounded portions, known as $A_1$, $A_2$, and $A_3$ for the anterior leaflet, and $P_1$, $P_2$ and $P_3$ for the posterior leaflet. The leaflets are attached to the papillary muscles by the chordae tendineae. The papillary muscles maintain the integrity of chordal leaflet alignment, preventing prolapse of the leaflets. The mitral valve allows blood to flow from the left atrium to the left ventricle but prevents blood from flowing back to the left atrium.

The tricuspid valve and the pulmonary valves are usually less affected by the disease process. Disease in the mitral valve and the aortic valve is more common in the affected adult population.

Mitral valve stenosis, for example, consists of an obstructive lesion to the leaflets of the valve. When the valves are narrow, also called "stenotic" valves, there is an obstruction to the flow of blood to the receiving chamber and an associated back up of blood. Dilatation of the left atrium develops and may be followed by right-sided heart failure and pulmonary edema, causing lung congestion and symptoms of shortness of breath. If the symptoms are severe, surgical intervention may be warranted.

Thickening and calcification is the commonest cause of narrowing of the mitral valve, secondary to the long-term effects of rheumatic disease. The incidence of mitral stenosis has decreased in the United States as the incidence of rheumatic fever has decreased as a result of the early institution of antibiotics. However, the leaking valve or the regurgitant valve incidence has increased in the last two decades. Mitral regurgitation is commonly due to degeneration or myxomatous disease leading to the lack of coaptation of the two mitral leaflets. The lack of coaptation in turn leads to the blood being regurgitated into the left upper chamber or the left atrium, causing pulmonary congestion and shortness of breath. Other causes include rupture of the chordae tendinea or the papillary muscles which are primarily needed to the support the two leaflets. Infection leading to the destruction of the valve leaflet or congenital clefts can also cause mitral regurgitation.

Treatments for these conditions have varied. Opening of the mitral valve was initiated in the 1950's in a closed method, known as a closed commisurotomy (separation of commisures by dialators). With the advent of heart-lung machine in 1955–56 by Dr. John H. Gibbons, Jr., open mitral comrnisurotomy was started with success.

Due to the high recurrence of stenosis, mitral valve replacement with prosthetic valves, typically constructed of a "ball and cage" (or ball valve), became the normal procedure in the 1960's, as proposed by Dr. Albert Starr. These valves were met with limited success as blood flow obstruction occurred with some frequency, leading to thromboembolism, causing strokes. Other attempts to replace the mitral valve were met with limited success. For example, Bjork Shiley valves were introduced as tilting disc valves to decrease the blood flow obstruction, but a flaw in the design led to strut fracture and their discontinuation. St. Jude valves, with a double tilting disc design, were introduced in the late 1970's. These valves have stood the test of durability and acceptable thromboembolism and are the preferred prosthetic valve replacement in the younger population.

Bioprothesis valves, harvested from heterologous mammals, such as swine and bovine, have also been successfully employed, however, such valves frequently wear out due to degeneration and calcification. Moreover, the current designs for the mitral valve are somewhat limited due to the specific VORTEX flow of the left ventricle. U.S. Pat. No. 6,074,417 illustrates a total bioprosthesis mitral valve.

When possible, surgical repair of the defective valve is preferable over the prosthetic replacement. The thrust of surgical repair has been to preserve the integrity of the papillary muscle, the chordae tendineae and the leaflets. Numerous studies have proved this hypothesis in terms of long-term results and the avoidance of anticoagulation, which can cause life-threatening bleeding complications. In the 1980's, Dr. A F Carpentier of France, pioneered several methods to repair the mitral valve. Rupture of the chordae or the prolapse of the middle scallop of the posterior leaflet was easily repaired by excising the diseased piece, repairing the annulas, and suturing the two leaflets. This procedure has become a preferred method and has produced consistent results. These repairs are supported by the placement of a cloth-covered metallic ring to bring the annulus to the near normal level.

Despite the advancement in the surgical management of the posterior leaflet, the repair of the anterior mitral leaflet has proven more difficult. Various surgical techniques have been devised, but without consistent results. Triangular resection of the leaflet, transposing part of the posterior leaflet to the anterior leaflet, chordal shortening have been proposed. Recently the use of the prosthetic material "goretex" sutures have been used as artificial chordae, with some early success. *Long Term Results of Mitral Valve Repair for Myxomatous Disease with and without Chordal Replacement with Expanded Polytetrafluoroethylee*, The Journal of Thoracic and Cardiovascular Surgery, June 1998, 1279–1286.

The use of prosthetic sutures for the anterior or posterior leaflet requires a great deal of skill on the part of the surgeon to make sure the sutures, duplicating the chords, are of the appropriate length. Moreover, attachment of the sutures to the leaflets and papillary muscles is delicate and cumbersome.

BRIEF SUMMARY OF THE INVENTION

The above discussed and other drawbacks and deficiencies are overcome or alleviated by a valve repair device having a leaflet portion, a muscle portion, and a plurality of chords connecting the leaflet portion to the muscle portion.

The valve repair device is attached to the diseased valve by suturing the leaflet portion to the affected leaflet and suturing the muscle portion to the affected muscle.

As an additional feature, the leaflet portion and muscle portion are constructed of cloth made from expanded polytetraflouroethylene. The chords are sutures also constructed from expanded polytetraflouroethylene.

As an additional feature, the leaflet portion or muscle portion include a reinforced attachment point for the sutures.

As an additional feature, the valve repair device may cut by the surgeon to eliminate unnecessary area in the leaflet, or to eliminate an excess number of chords.

BRIEF DESCRIPTION OF THE DRAWINGS

Referring to the FIGURES wherein the like elements are numbered alike in the several FIGURES

DETAILED DESCRIPTION OF THE DRAWINGS

Figure 1:
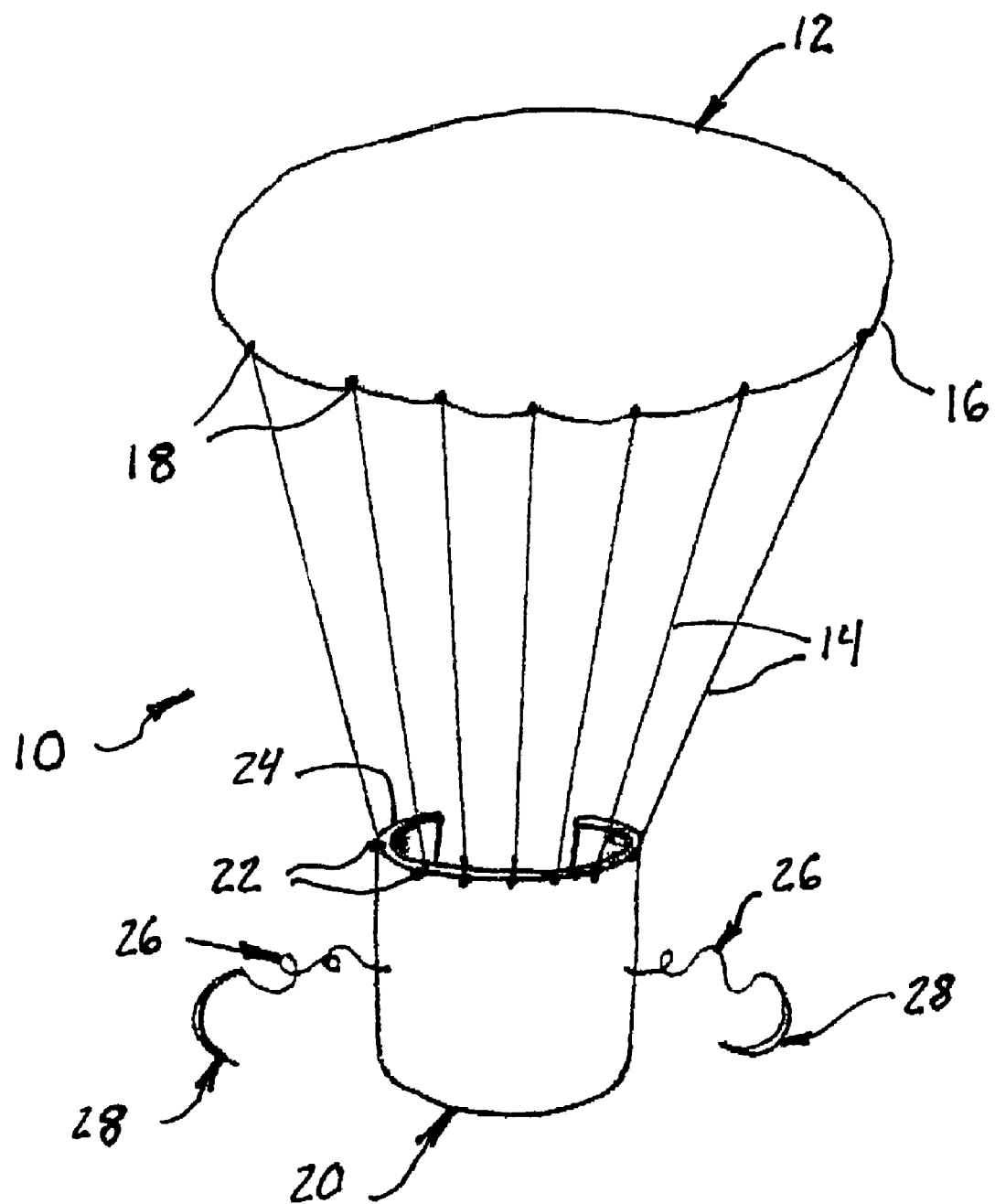
FIG. 1 shows a prospective view of the valve repair device.

Referring to FIG. 1, a valve repair device 10 in accordance with the present invention is illustrated. Valve repair device 10 includes a leaflet portion 12. A plurality of chords 14 extend from the leaflet portion 12 and are attached to the leaflet portion 12 adjacent end 16 at a plurality of attachment locations 18. Chords 14 connect leaflet portion 12 to a muscle portion 20 at a plurality of respective attachment locations 22 adjacent end 24 of muscle portion 20.

Leaflet portion 12 is a thin flexible element preferably constructed of a biocompatible cloth. Preferably, leaflet portion 12 is constructed of a plastic reinforced cloth, such as expanded polytetraflouroethylene. Gor-Tex®, produced by W. L. Gore and Associates, Inc., Flagstaff, Ariz., is an example of a suitable biocompatible cloth made from expanded polytetraflouroethylene. Leaflet portion 12 provides an anchor to the leaflet of a valve of the heart for chords 14, and may essentially replicate the leaflet, if the leaflet is diseased. Chords 14 are preferably constructed from suture material, such as expanded polytetraflouroethylene, such as GorTex® 5-0 ePTFE and/or 6-0 ePTFE. Leaflet portion 12 is sized for repair of the anterior or posterior leaflet, and more specifically, to cover excised diseased material, such as after a resection of a segment of a floppy valve, either a posterior or anterior leaflet. End 16 may be rounded as the posterior and anterior leaflets are scalloped shaped. More preferably, leaflet portion 12 is rounded at its outer periphery, in a similar manner to the natural leaflets.

Muscle portion 20 is likewise a flexible element and preferably constructed of a biocompatible cloth. Preferably, muscle portion 20 is constructed of expanded polytetraflouroethylene, such as Gor-Tex®. Muscle portion 20 has a rounded portion 24, and is sized to be attached to the papillary muscle of the heart. Muscle portion 20 provides an anchor for chords 14 to the papillary muscle. Muscle portion includes a pair of sutures 26 attached to muscle portion 20, with needles 28 attached at the free end of the sutures 26. Muscle portion 20 may be cylindrically shaped to surround the papillary muscle.

Chords 14 connect leaflet portion 12 and muscle portion 20 and function as the chordae tendineae as explained in greater detail below. Chords 14 are sewn to leaflet portion 12 and muscle portion 20 at respective attachment locations 18 and 22, and maybe reinforced by weaving chords 14 into the weave pattern of leaflet portion 12 and muscle portion 20. Alternatively, chords 14 may be fastened on leaflet portion 12 or muscle portion 20, such as with a plastic clip or as a contiguous part of the cloth or prosthetic material.

Figure 2:
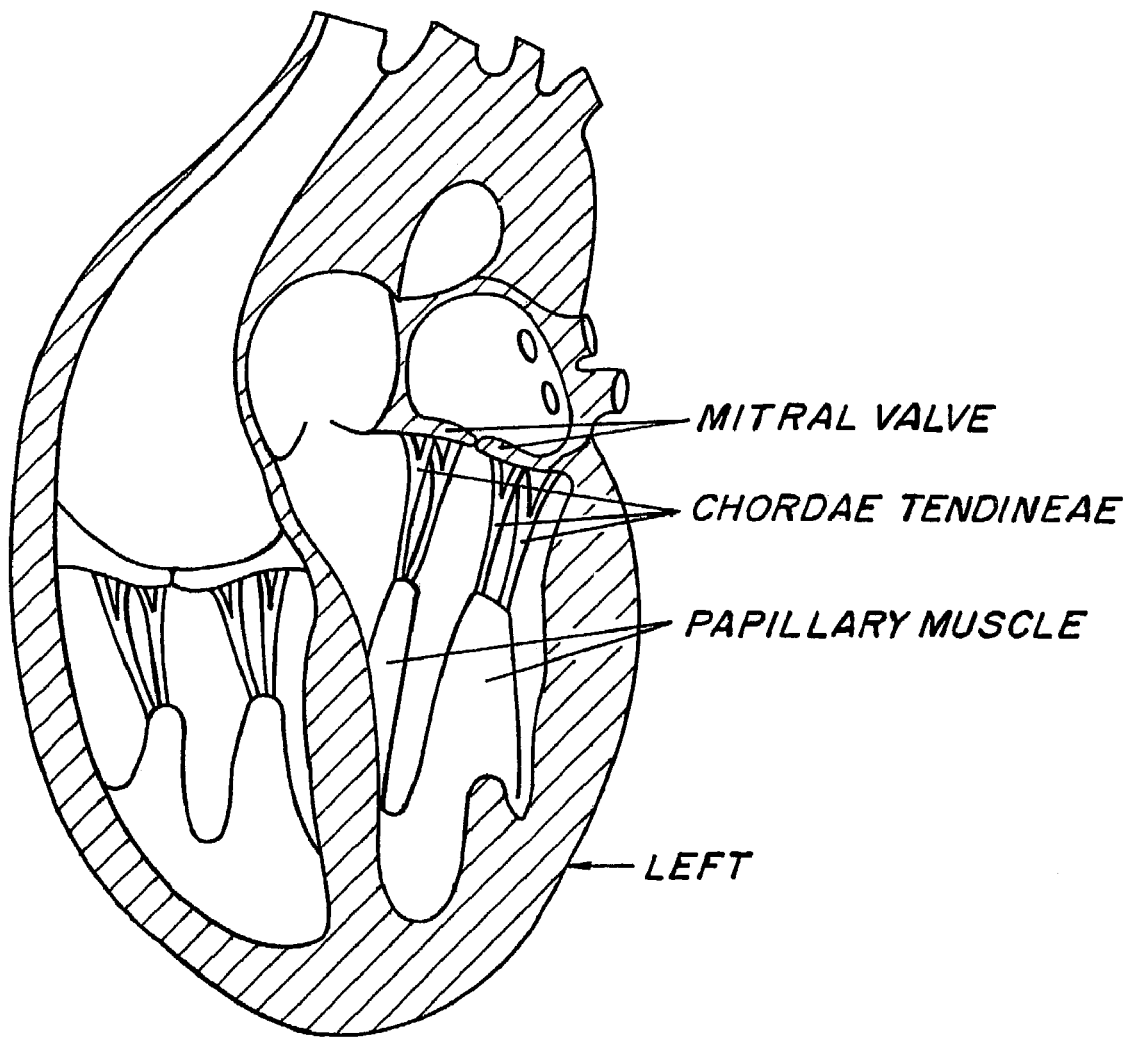
FIG. 2 illustrates a prior art cross sectional view of the heart, illustrating the mitral valve of the heart.
Figure 3:
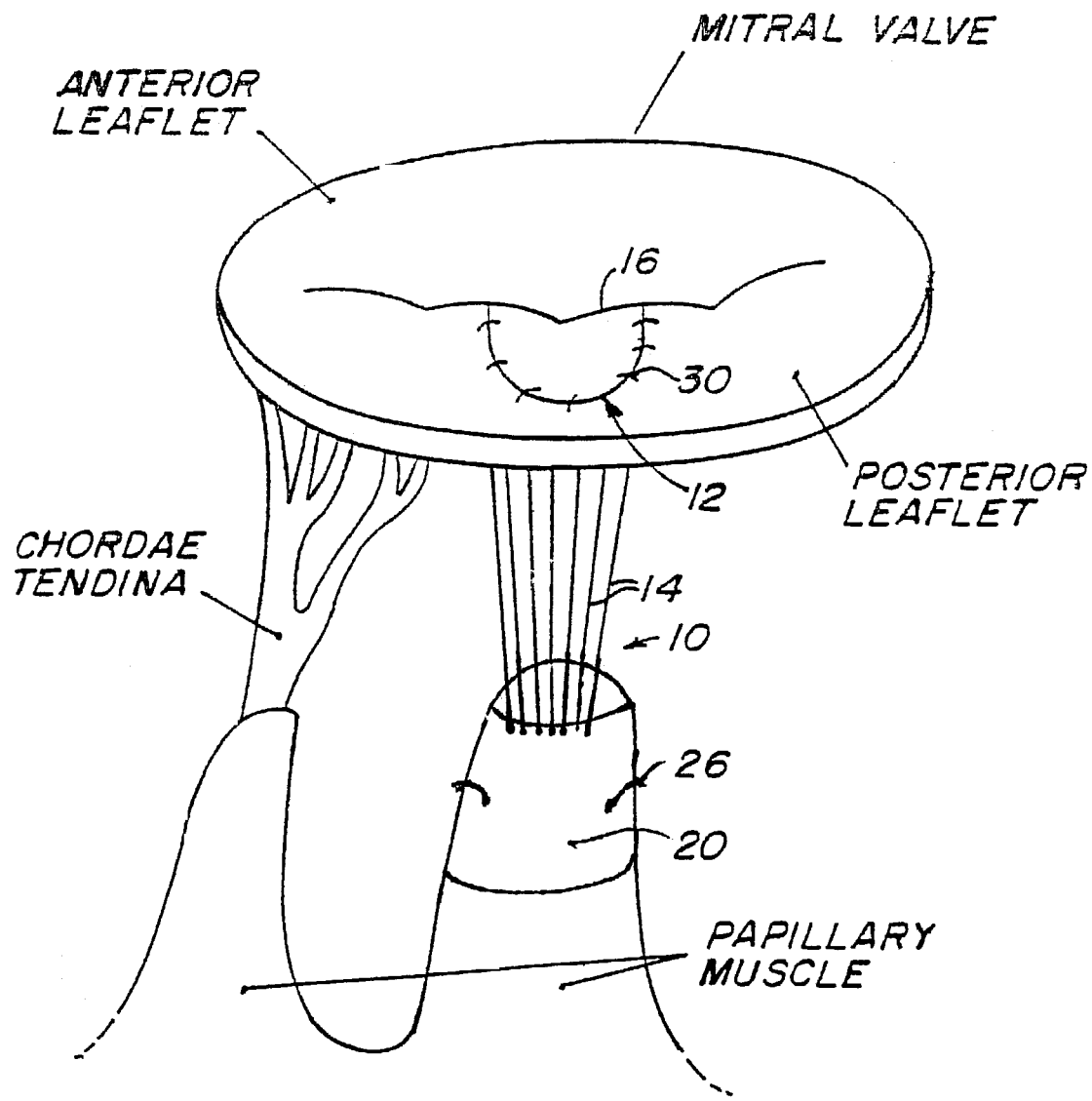
FIG. 3 shows a perspective view of the valve repair device sutured in the mitral valve.

Referring to FIGS. 2 and 3, the repair of the posterior leaflet of the mitral valve of the heart with valve repair device 10 is illustrated. As shown in prior art FIG. 2, the chordae tendineae are attached to the respective posterior leaflet or anterior leaflet and connect the leaflet to the papillary muscle. During a typical repair of the mitral valve, the diseased portion of the valve is excised, such as the elongated portion of a chordae or a ruptured chordae, and the remaining leaflet material is then sutured together. If the chordae tendoneae is diseased, it may also be excised, with sutures connecting the leaflet to the papillary muscle. As shown in FIG. 3, and in accordance with the present invention, valve repair device 10 is directly sutured to the mitral valve with suture 30 attaching leaflet portion 12 along its outer periphery to the affected leaflet and sutures 26 attaching muscle portion 20 to the affected papillary muscle so that chords 14 replicate the chordae tendineae. Leaflet portion 12 is sutured over the excised diseased material with sutures 30, thereby reducing the impact to the leaflet and its function that is associated with the prior art method of reconnecting the leaflet at the point of excision.

Figure 4:
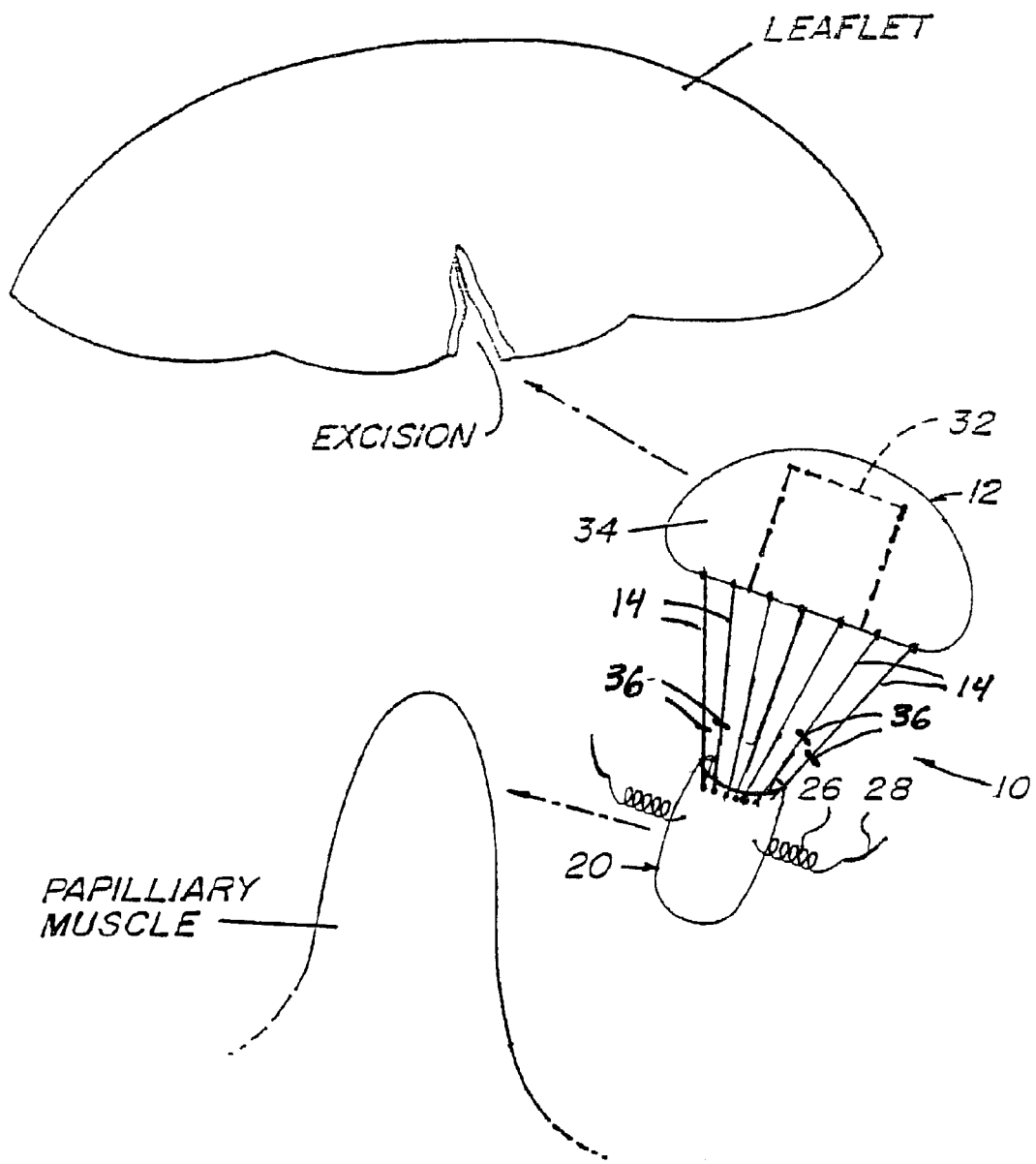
FIG. 4 shows an exploded view of the placement of the valve repair device to the repair site of an affected leaflet.

Turning now to FIGS. 3 and 4, during open-heart surgery, the physician will assess the degree of disease, and determine the extent of the repair to the mitral valve needed. The surgeon will first excise the diseased material, such as the elongated scallop portion of a leaflet, the perforated portion of the leaflet, the affected chordae tendineae, etc. An annular ring may be used to reinforce the mitral valve. Next, the surgeon will determine the size of the valve repair device 10 needed to effectuate the repair and may reduce leaflet 12 by cutting, such as illustrated by line 32, unneeded area 34 from leaflet portion 12. The physician also cuts unneeded chords 14, such as illustrated by lines 36.

Figure 5:
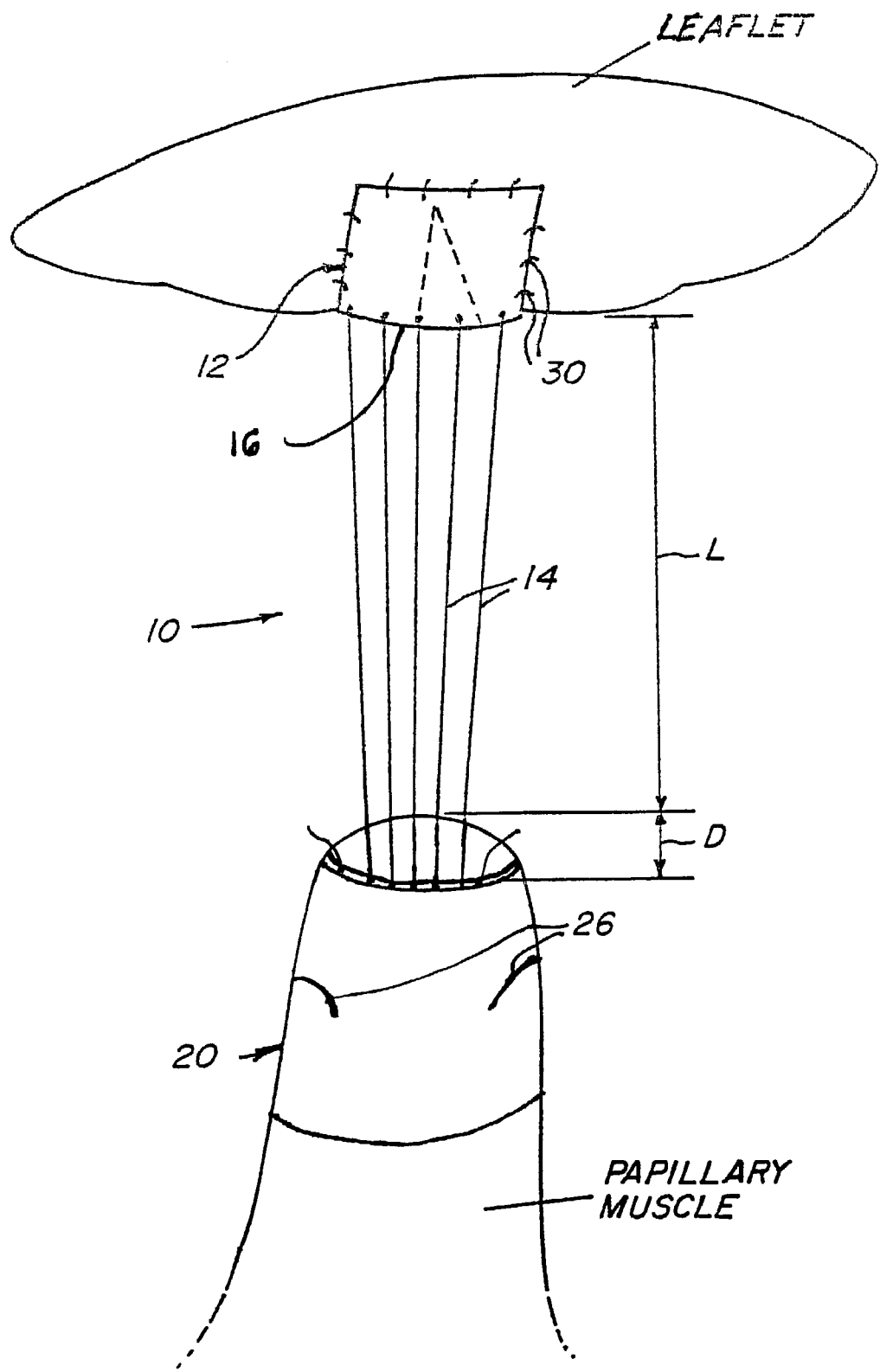
FIG. 5 shows a perspective view of the valve repair device sutured to an affected leaflet and papillary muscle.
Figure 5A:
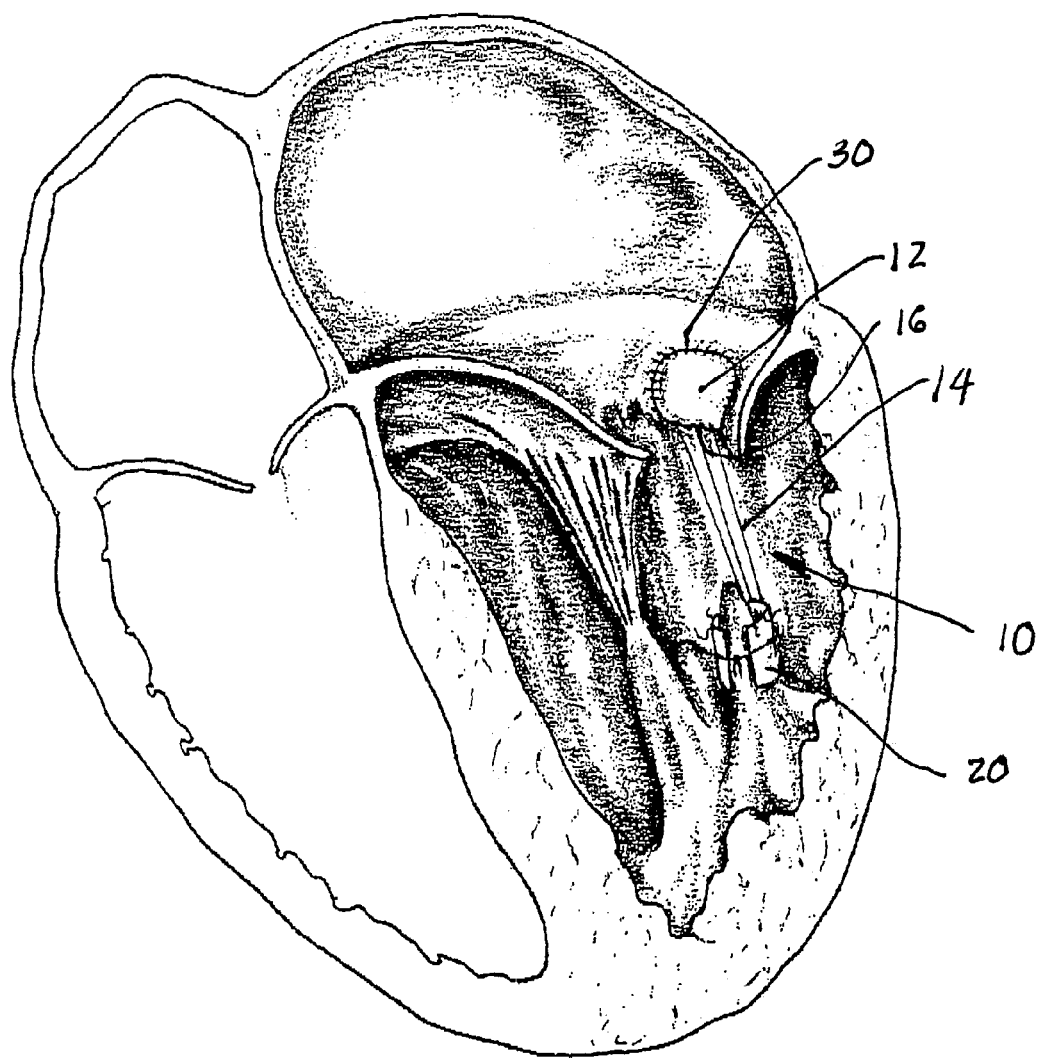
FIG. 5a shows a perspective view of the valve repair device sutured to an affected leaflet and papillary muscle in the heart.

Referring to FIGS. 5 and 5a, the surgeon sutures leaflet portion 12 over the affected area of the posterior or anterior leaflet with sutures 30 such that end 16 is positioned near the edge of the leaflet. Next, the surgeon sutures muscle portion 20 to the papillary muscle with sutures 26. Prior to suturing muscle portion 20 to the papillary muscle, the surgeon must determine the distance or location, as illustrated by dimension D, to achieve an effective repair such that the leaflets will open and close effectively. It is important that the leaflet be spaced at a length, as illustrated by dimension L, from the papillary muscle so that the leaflet is positioned properly to open and close effectively. Failure to accurately determine the location for muscle portion 20 may result in an ineffective repair, causing prolapse of the leaflet, which in turn may cause the valve to leak.

In order to accurately determine the location, as illustrated by dimension D, the surgeon may estimate the needed chord length by comparing the relative length of the adjoining chords. The chordae tendeneae comprise the marginal chord, the secondary chord and the basilar chord. The marginal chord is located adjacent the margin or edge of the respective anterior or posterior leaflet. The basilar chord is located adjacent to the area adjoining the annulus of the mitral valve and the secondary chord is positioned between the marginal chord and the basilar chord. Disease in the mitral valve is typically associated with the marginal chord. Subsequent to its removal, the surgeon may approximate the needed chord length, as illustrated by dimension L, by positioning the valve repair device adjacent to a normal marginal chord. The surgeon may also reference the chord length of the opposing anterior or posterior leaflet chordae tendeneae. Preferably, the surgeon will suture a holding stitch or a stay suture between the anterior and posterior leaflets at the level of adjoining normal chordae to obtain accurate approximation of the desired chord length. In this manner, the surgeon may suture muscle portion 20 to the papillary muscle at a distance D to achieve the desired location to effectuate a repair.

It should be understood by those of ordinary skill in the art that the surgeon could suture muscle portion 20 to the papillary muscle with sutures 26 and then suture leaflet portion 12 to the leaflet with sutures 30, provided that the location of leaflet portion 12 and muscle portion 20 allows the leaflets to open and close effectively.

Figure 6:
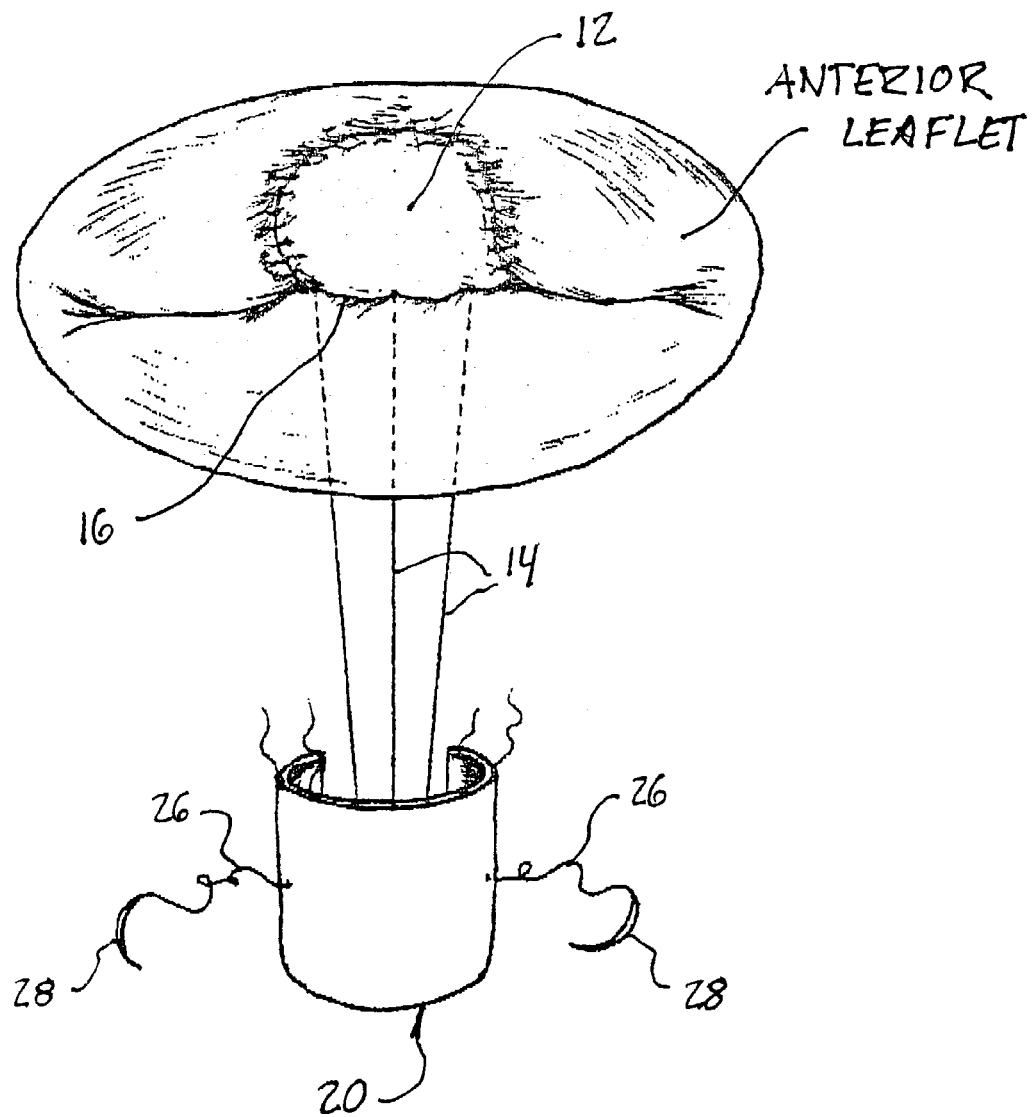
FIG. 6 shows a perspective view of the valve repair device sutured to the anterior leaflet.
Figure 7:
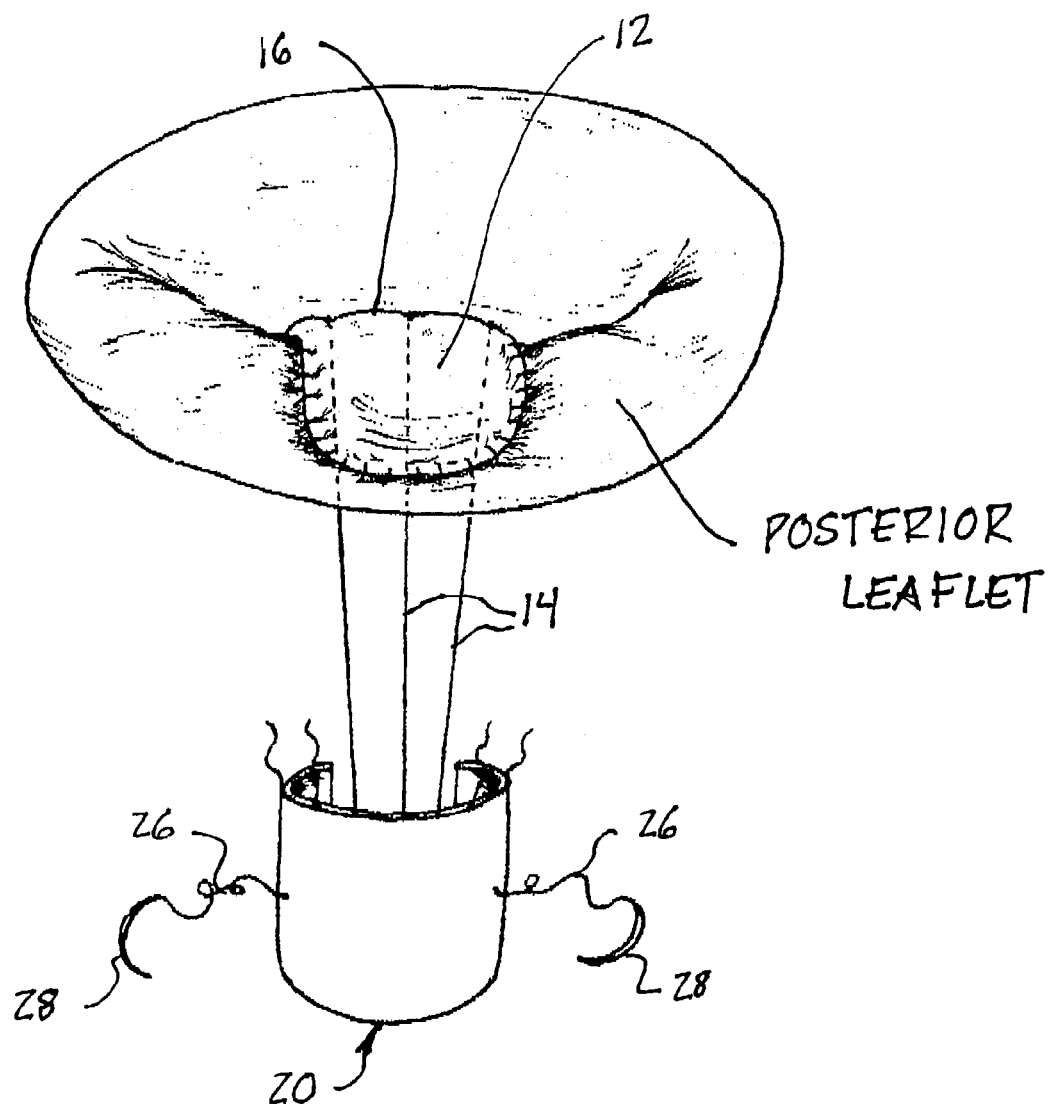
FIG. 7 shows a perspective view of the valve repair device sutured to the posterior leaflet.

As illustrated in FIGS. 6 and 7, valve repair device 10 may be used to repair the anterior leaflet or the posterior leaflet, by positioning leaflet portion such that end 16 is positioned along the outer edge of the leaflet to be repaired. Moreover, valve repair device 10 may be offered in a variety of sizes and specifically in a kit form. Prior to undertaking the repair of the mitral valve, the surgeon will typically be acquainted with patient's specific physiology. During the open-heart operation, time is an important factor, and a surgeon may be confronted with an unknown defect in the valve. In use, valve repair device 10 eliminates the bulky process of affixing sutures from the papillary muscle to the respective posterior or anterior leaflet. Leaflet portion 12 is sutured directly to the leaflet with sutures 30, and muscle portion 20 is sutured directly to the papillary muscle with sutures 26. The surgeon may easily modify the size of valve repair device 10 by cutting excess areas from leaflet 12 and/or muscle portion 20, saving time. Moreover, the ease of attaching leaflet portion 12 to the leaflet as well as attaching muscle portion 20 to the papillary muscle increases the surgeon's ability to obtain the effective opening and closure of the valve, as the tedious and more imprecise process of attaching sutures as chords is eliminated. The anterior leaflet of the mitral valve is particularly difficult to repair given its proximity to the aortic valve. The instant invention allows the surgeon to suture leaflet portion to the anterior leaflet without affecting the aortic valve.

Figure 8:
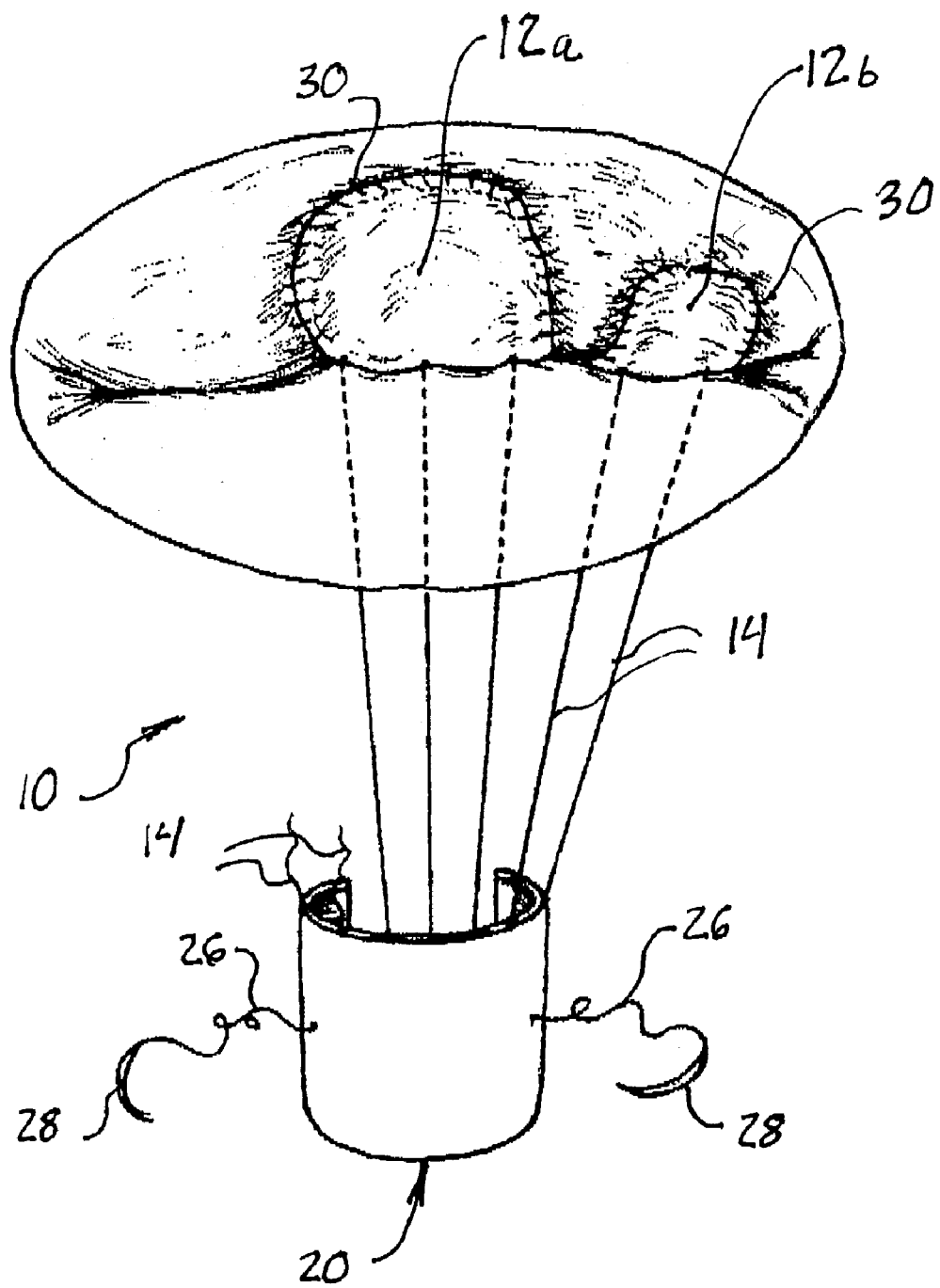
FIG. 8 shows a prospective view of another use of the valve repair device.

Referring now to FIG. 8, another use of valve repair device 10 is illustrated. In use, the surgeon may encounter a leaflet with multiple diseased areas but which is stable enough to sustain a repair as opposed to a total replacement of the mitral valve. Leaflet portion 12 is cut for application to the affected areas. Leaflet portion 12 may be cut into separate parts, 12a and 12b, as shown, with each part connected to muscle portion 20 by chords 14. Leaflet portions 12a and 12b are sutured to the affected areas of the leaflet to be repaired with suture 30. Unnecessazy chords 14 may be cut by the surgeon. Muscle portion 20 is attached to the papillary muscle as previously discussed above.

Figure 9:
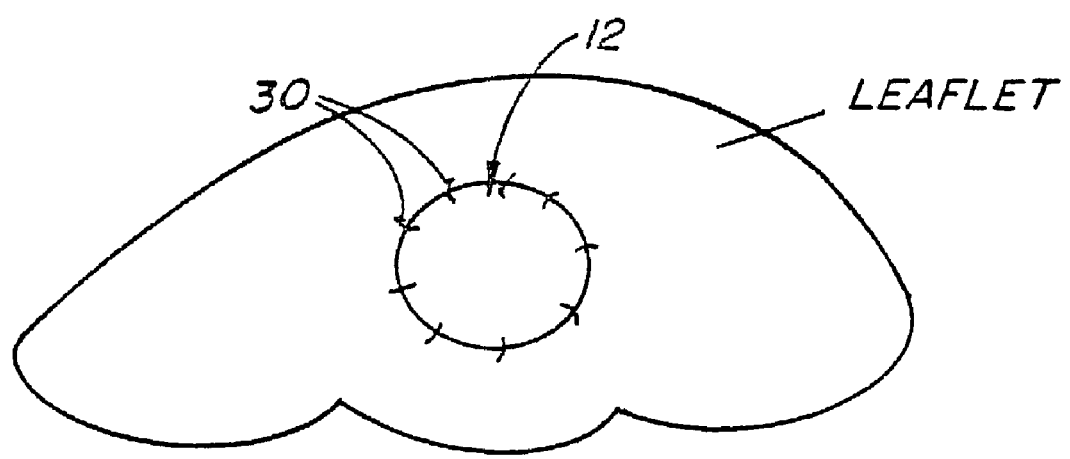
FIG. 9 shows a prospective view of another use of the valve repair device.

As shown in FIG. 9, another use of valve repair device 10 is illustrated. Leaflet portion 12 has been cut to effectuate the repair of a healed perforation of a leaflet secondary to endocorditis. In this use chords 14 and muscle portion 20 have been removed from leaflet portion 12. Leaflet portion 12 has been sutured over the perforation with suture 30.

Figure 10:
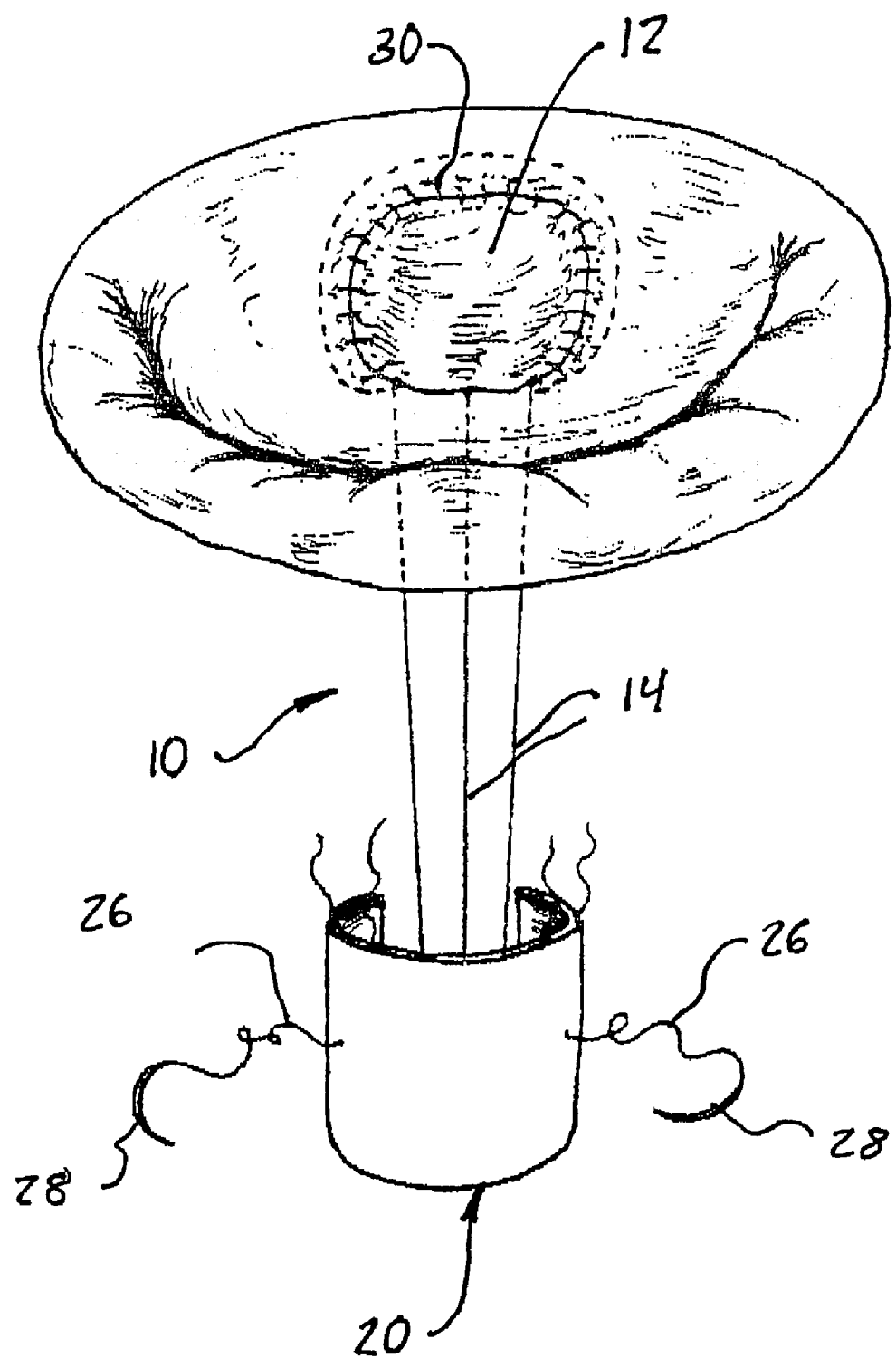
FIG. 10 shows a prospective view of another use of the valve repair device.

Turning now to FIG. 10, another use of valve repair device 10 is illustrated. Leaflet portion 12 has been cut to effectuate the repair of a healed perforation of a leaflet secondary to endocorditis. Chords 14 remain attached to leaflet portion 12 and connect leaflet portion 12 to muscle portion 20. Leaflet portion 12 is sutured over the perforation with suture 30 along most of the periphery of the cut leaflet portion 12. Muscle portion 20 is attached to the papillary muscle with sutures 26.

Figure 11:
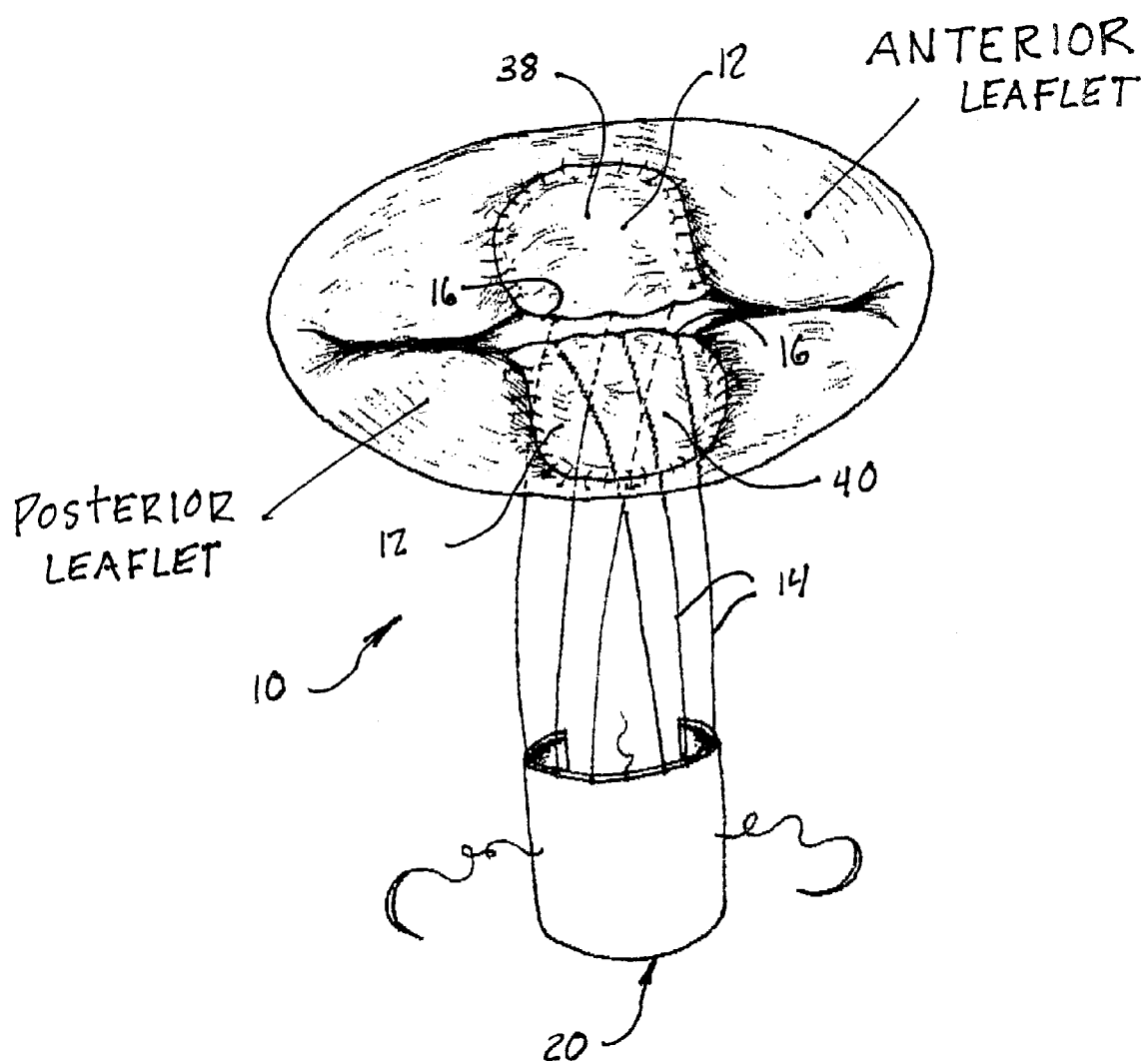
FIG. 11 shows a prospective view of another use of the valve repair device.

Referring now to FIG. 11, another use of valve repair device 10 is illustrated. It will be appreciated that a surgeon may be presented with a patient having disease in both the anterior leaflet and posterior leaflet which lends itself to a dual repair of the anterior leaflet and the posterior leaflet. In this use, leaflet portion 12 is cut by the surgeon into two pieces 38 and 40, as shown. Piece 38 is folded such that end 16 is position along the edge of the anterior leaflet. Piece 40 is folded such that end 16 is positioned along the edge of the posterior leaflet. After sutured pieces 38 and 40 to the respective leaflets, the surgeon may position the valves in the closed position and approximate the needed chord length by positioning the valve repair device adjacent to the secondary or basilar chord, as discussed above. The surgeon may also employ a stay stitch to temporarily connect muscle portion 20 to the papillary muscle.

Figure 12:
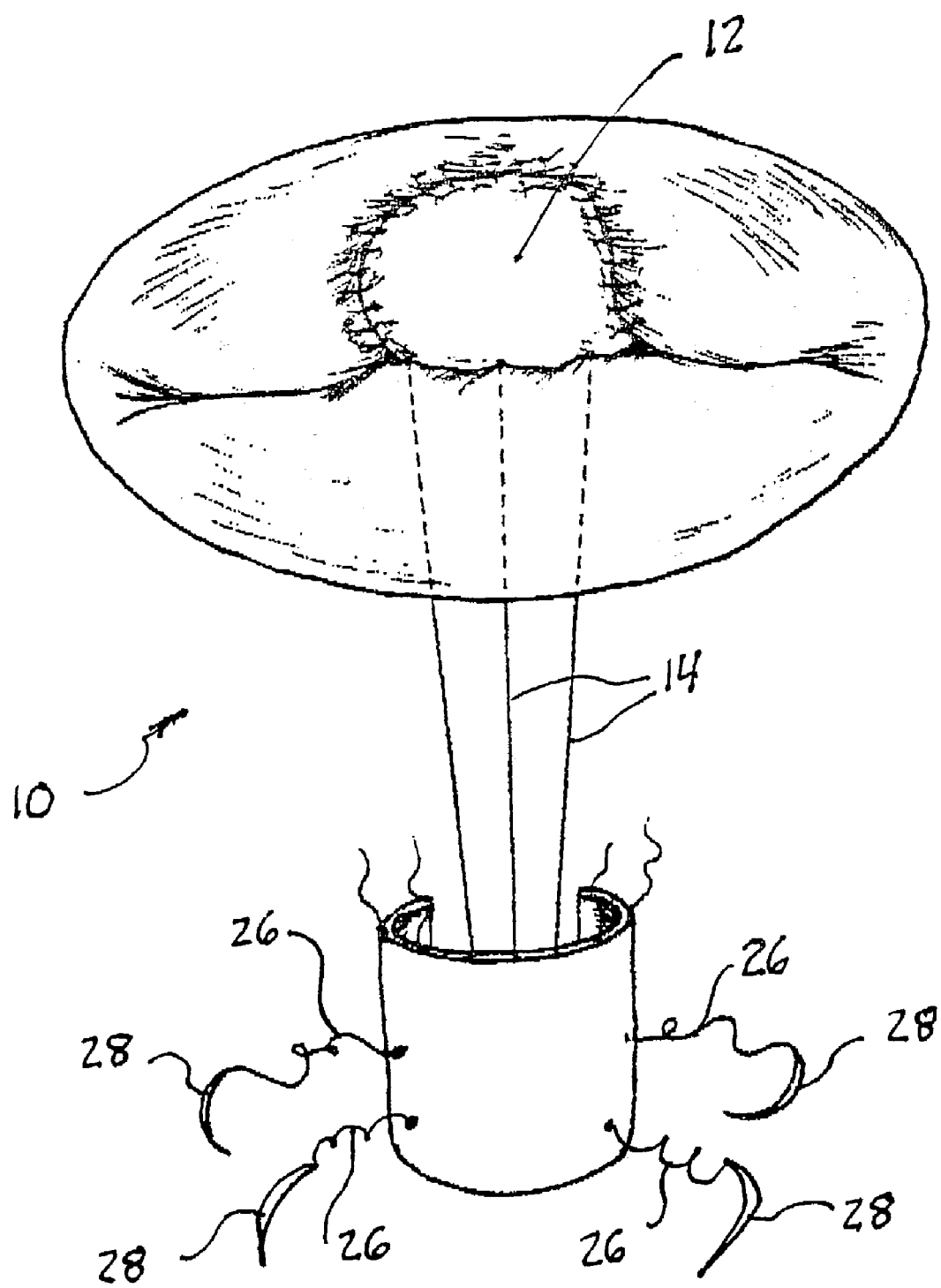
FIG. 12 shows another embodiment of the valve repair device.

As shown in FIG. 12, another embodiment of valve repair device 10 is illustrated. Valve repair device 10 includes leaflet portion 12, chords 14, and muscle portion 20 as in the first embodiment. Is this embodiment, two pairs of attached sutures 26 with needles 28 are provided for attachment of muscle portion 20 to the papillary muscle. It will be appreciated by those of ordinary skill in the art that additional sets of sutures 26 and needles 28.

Figure 13:
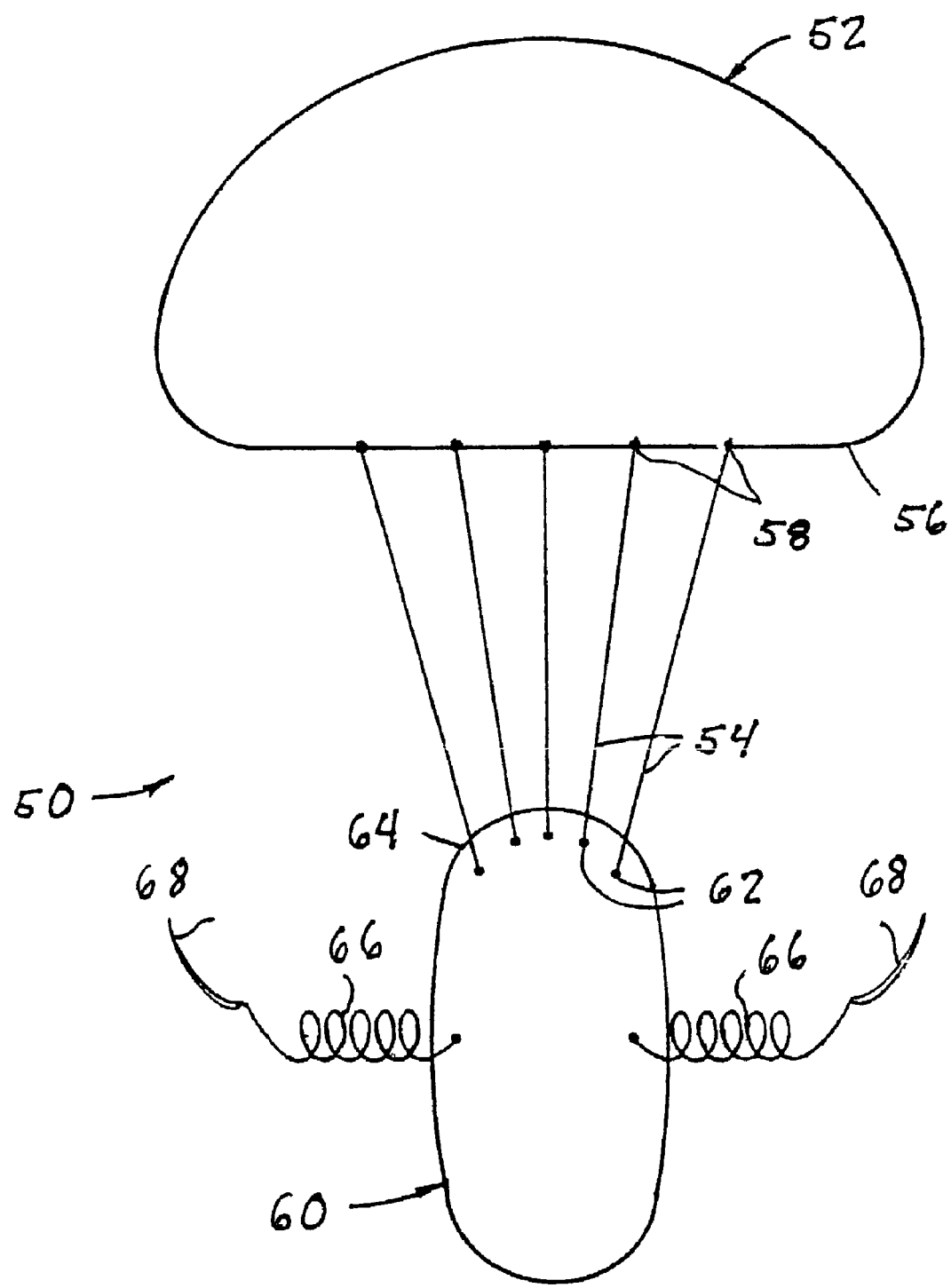
FIG. 13 shows another embodiment of the valve repair device

As shown in FIG. 13, another embodiment of the valve repair device is shown at 50. Valve repair device 50 includes a leaflet portion 52. A plurality of chords 54 extend from the leaflet portion 52 and are attached to the leaflet portion 52 adjacent end 56 at a plurality of attachment locations 58. Chords 54 connect leaflet portion 52 to a muscle portion 60 at a plurality of respective attachment locations 62 adjacent end 64 of muscle portion 60. Muscle portion includes a pair of sutures 66 attached to muscle portion 60, with needles 68 attached at the free end of the sutures 66. Muscle portion 60 is sutured to the papillary muscle along a portion of the muscle. Leaflet portion 52 and muscle portion 60 are made of a flexible material, as described above.

While the invention has been described with reference to a preferred embodiment, it will be understood by those skilled in the art that various changes may be made and equivalents may be substituted for elements thereof without departing from the scope of the invention. In addition, many modifications may be made to adapt the invention to a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A device for repair of a valve of a heart comprising:
 a first portion, said first portion comprising a flexible element, said flexible element having an outer periphery, said outer periphery having an attachment area,
 a second portion, said second portion comprising a flexible element,
 at least one chord, said chord having opposite ends, one of said ends being attached to said first portion, the other of said ends being attached to said second portion,
 a first suture adapted to connect said first portion at least partially along said outer periphery at said attachment area to the native leaflet of a heart valve, wherein said first portion is configured to at least partially cover an opening, wound or defect in said leaflet, and
 a second suture adapted to connect said second portion to the papillary muscle of a heart.

2. The device of claim 1, wherein said first portion comprises a cloth made of expanded polytetraflouroethylene.

3. The device of claim 1, wherein said at least one chord is a plurality of chords, each of said chords having opposite ends, one of each said ends being attached to said first portion, the other of each said ends being attached to said second portion.

4. The device of claim 3, wherein said chords being attached at one of each said ends to said first portion adjacent said outer periphery.

5. The device of claim 4, wherein said outer periphery is rounded.

6. The device of claim 3, wherein said chords are sewn to said first portion and to said second portion.

7. The device of claim 3, wherein said second suture is affixed at a first end to said second portion.

8. The device of claim 1, wherein said at least one chord are made of expanded polytetraflouroethylene.

9. The device of claim 1, wherein said outer periphery of said first portion is rounded.

10. The device of claim 1, wherein said second portion comprises a cloth made of expanded polytetraflouroethylene.

11. A method for repairing a heart valve, comprising:
 providing a device for repairing a heart valve, said device having a first portion, said first portion comprising a flexible element, said flexible element having an outer periphery, said outer periphery having an attachment area,
 a second portion, said second portion comprising a flexible element, at least one chord, said chord having opposite ends, one of said ends being attached to maid first portion, the other of said cads being attached to said second portion;
 suturing said first portion at least partially along said outer periphery to the native leaflet of a valve at said attachment area, wherein said first portion at least partially covers an opening, wound or defect in said leaflet; and
 suturing said second portion to a papillary muscle.

12. The method of claim 11 further comprising removing part of said first portion prior to suturing said first portion to the leaflet.

13. The method of claim 11 further comprising removing part of said chord prior to suturing said first portion to the leaflet.

14. The method of claim 11, wherein said first portion comprises a cloth made of expanded polytetraflouroethylene.

15. The method of claim 11, wherein said at least one chord is a plurality of chords, each of said chords having opposite ends, one of each said ends being attached to said first portion, the other of each said ends being attached to said second portion.

16. The method of claim 11, wherein said at least one chord being attached at one of each said ends to said first portion adjacent said outer periphery.

17. The method of claim 11, wherein said at least one chord are sewn to said first portion and to said second portion.

18. The method of claim 11, wherein said second portion comprises a suture having a first end attached to said second portion and a second end having a needle attached thereto.

19. The method of claim 11, wherein said first portion includes a rounded edge, said edge being attached adjacent to the scalloped edge of the leaflet.

20. The method of claim 11, wherein said outer periphery is rounded.

* * * * *